United States Patent [19]  [11] 4,305,406
Megahed  [45] Dec. 15, 1981

[54] NEEDLE ASSEMBLIES WITH ANTI-BACKFLOW FEATURES

[75] Inventor: Shenoda S. Megahed, Lyndhurst, N.J.

[73] Assignee: Becton, Dickinson and Company, Paramus, N.J.

[21] Appl. No.: 159,084

[22] Filed: Jun. 13, 1980

[51] Int. Cl.³ .............................................. A61B 5/14
[52] U.S. Cl. ............................. 128/766; 128/218 NV
[58] Field of Search ......................... 128/766, 218 NV

[56] References Cited
U.S. PATENT DOCUMENTS

| | | | |
|---|---|---|---|
| 3,848,579 | 11/1974 | Villa-Real | 128/766 |
| 3,996,923 | 12/1976 | Guerra | 128/766 |
| 4,066,079 | 1/1978 | Chiarolla | 128/218 NV |
| 4,106,497 | 8/1978 | Percarpio | 128/766 |
| 4,244,379 | 1/1981 | Smith | 128/766 |

Primary Examiner—John D. Yasko
Attorney, Agent, or Firm—Richard J. Rodrick

[57] ABSTRACT

A needle assembly for use in preventing backflow of blood being collected from a patient comprises a housing with a chamber therein, and including first and second access openings through the housing in fluid communication with the chamber. A cannula extends outwardly from the first access opening and is adapted for insertion into a patient. The chamber has a volume sufficiently large to store blood therein collected from the patient and to delay blood from backflowing from the second access opening into the first access opening under normal patient blood flow conditions due to the large amount of blood which must first be displaced from the chamber.

In another embodiment of the present invention, the chamber includes flow resistance elements positioned in the chamber to provide flow resistance in the flow of blood from the chamber toward the first access opening. These objects may include tapered cones to favor flow of blood in one direction but not the other direction.

2 Claims, 7 Drawing Figures

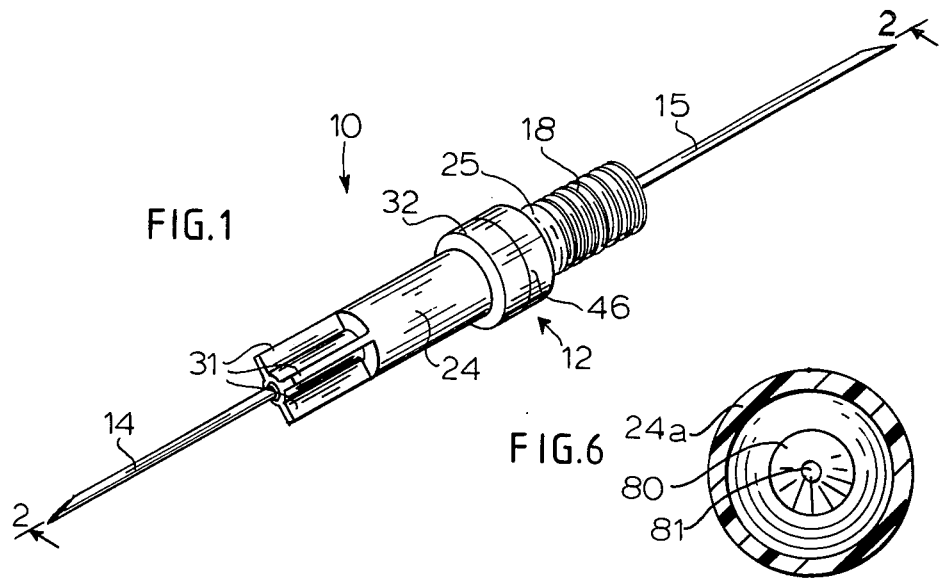
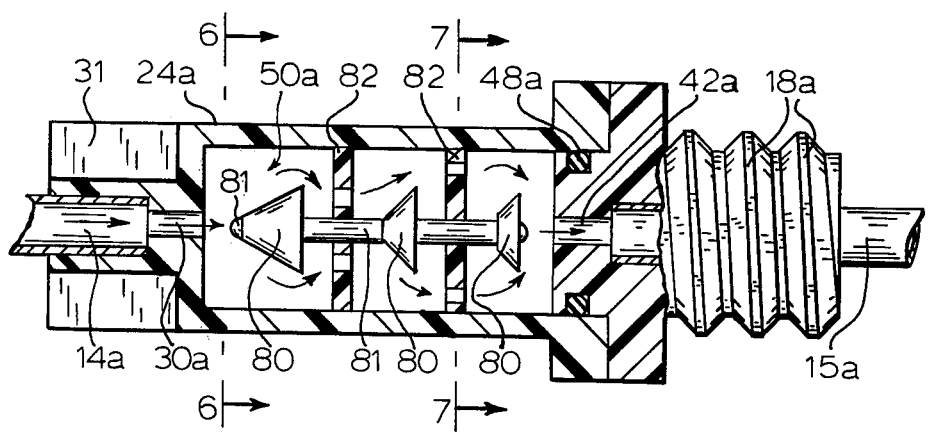

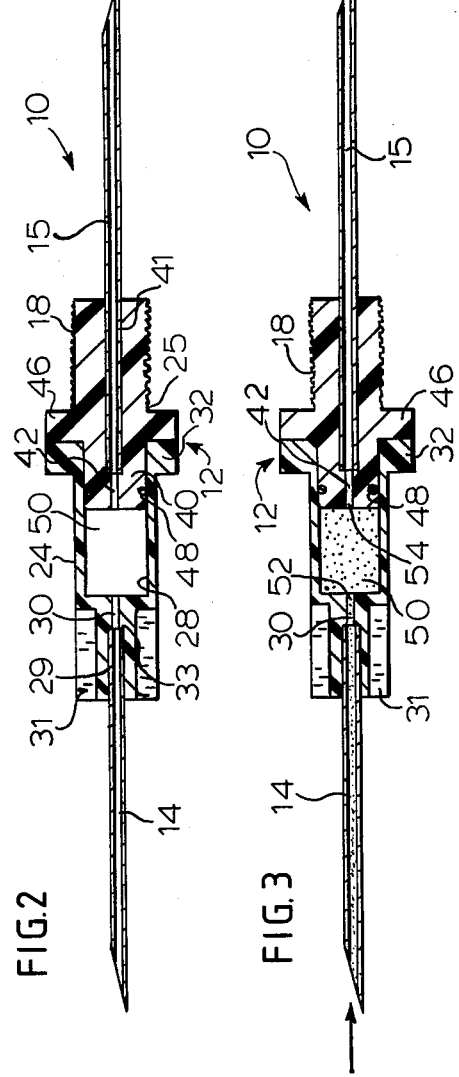
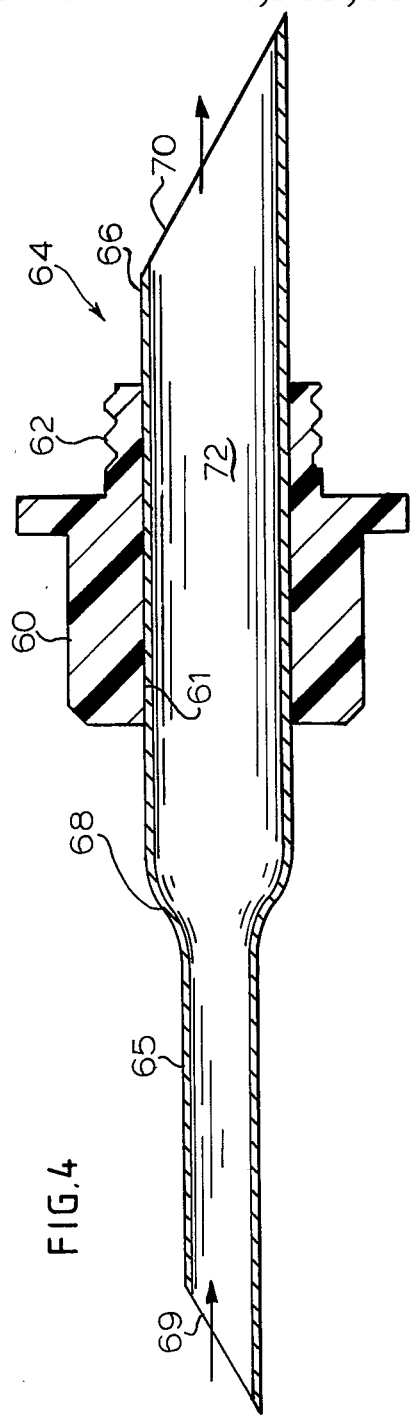
FIG.2
FIG.3
FIG.4

NEEDLE ASSEMBLIES WITH ANTI-BACKFLOW FEATURES

BACKGROUND OF THE INVENTION

The present invention relates to needle assemblies with anti-backflow features, and more particularly, concerns such a needle assembly with anti-backflow characteristics without the inclusion of an operative valve or like device within.

In the collection of fluids, and especially when such fluids may be blood or other bodily fluids from a patient, it is highly desirable that backflow into the patient be prevented, or at least delayed for a substantially long time period. The reasons for prevention of fluid back into the patient are numerous. For example, when collecting blood into a collection container, various chemicals or other reagents may be present in the container for different tests on the blood sample. As the blood sample flows into this container, it mixes with the chemical therein. Should this mixture backflow into the patient, the chemical would then enter the patient's blood stream with potential harm to the patient. Another instance where backflow into the patient could be problematical involves clotting of the blood during the collection procedure. Should a small amount of the collected blood clot somewhere in the collection needle or container, backflow of such a clotted or coagulated amount of blood into the patient could cause serious difficulties. Accordingly, the inclusion of some type of anti-backflow mechanism into a needle assembly for the collection of fluids from a patient is a desired feature.

In prior attempts at controlling this undesirable backflow of blood or bodily fluid, reliance has been placed particularly on the use of various types of valves. These valves have been proposed in various shapes and forms, notably including shiftable ball valves, cup valves, disk valves with a self-sealing slit therein, "duck bill" valves and the like which open and close under differential fluid pressures. Other types of valves may also have been proposed. These valves are all based on an operative component whereby either fluid pressure, needle puncture, or force of the moving fluid causes the valve to open and close depending upon the respective direction of fluid flow. In addition to the expense of manufacture involved in these small, somewhat intricate valve devices, the difficulty involved in mounting the same into a small needle assembly and attendant problems in handling the same, an operative valve of this nature takes on another risk, namely involving its functionability. When reliance is placed upon an operating valve, there must be significant assurance that the valve will operate according to its intended purpose and design. If the valve fails to operate, then backflow of blood or other bodily fluid into the patient will not be prevented. Therefore, with such an operative element included in the needle assembly, it must be concluded that there is always a risk that the valve will not operate properly with potential harmful consequences. Therefore, a straightforward mechanism for preventing or, at least, delaying backflow of blood or the like fluids into a patient during the blood collecting procedure is still being sought. This mechanism is one which not only will operate effectively, but minimize or completely eliminate the attendant risk involved with operative valves as described above. It is to the solution of this problem which the present invention is directed.

SUMMARY OF THE INVENTION

A needle assembly for use in delaying backflow of blood being collected from a patient comprises a housing having a forward end, a rearward end and a chamber therein. A first access opening through the forward end of the housing is in fluid communication with the chamber. A cannula extends outwardly from the first access opening in fluid communication with the chamber and is adapted for insertion in a patient. A second access opening through the rearward end of the housing is in fluid communication with the chamber and is adapted for communication with collection means for receiving said blood. The chamber has a volume being sufficiently large to store blood therein collected from the patient and to delay blood from backflowing from the second access opening into the first access opening under normal patient blood flow conditions due to the large amount of blood which must first be displaced from the chamber.

In the preferred embodiment of this aspect of the invention, the chamber has a volume between four hundred (400) and six hundred (600) cubic millimeters, and has a larger cross-sectional dimension than the cross-sectional dimensions of the first and second access openings immediately adjacent the chamber.

In another aspect of the present invention, the chamber and the patient insertion cannula are formed of an integrally connected structure. Preferably, this structure is a dual diameter needle structure, with the smaller diameter needle extending outwardly for insertion into the patient. The larger diameter portion of this needle serves as both a collection chamber and as a second cannula extending oppositely from the housing and adapted for insertion into an evacuated blood collection container. The larger diameter portion of the cannula provides enough internal volume to act as a storage compartment to thereby delay ready backflow of blood into the patient.

In still another aspect of the present invention, the chamber includes means positioned therein to provide flow resistance in the flow of blood from the chamber toward the first access opening. The flow resistance means may include a plurality of substantially rigid, non-operative objects within the chamber to limit the flow area of blood therein. These non-operative objects preferably include tapered cones substantially centrally mounted in the chamber along a longitudinal axis with sufficient annular clearance for blood to flow therearound. These cones are positioned so that their narrow, tapered portions face toward the first access opening whereby flow of blood is favored in the direction from the first access opening into the chamber and is resisted in the opposite direction.

From the structural standpoint, the present invention is notably different from prior needle assemblies with anti-backflow features. In particular, the present invention offers anti-backflow features without the inclusion of operative elements therein. In other words, there are no movable, shiftable, open/close elements, gate-like devices included in this invention. By eliminating an operative type of flow valve, all the attendant deficiencies are also removed. As a result, the risks that the needle assembly may not operate as intended are also concurrently eliminated or substantially diminished. The present invention serves to provide fluid backflow delay means by relying upon the storage of a large amount of fluid, the flow direction of which cannot be readily changed without first depleting almost all of this large amount of stored fluid. This concept, while at first blush appearing to be simple, nevertheless, is effective when taking into account the normal type of blood flow conditions during the typical blood collecting procedure. In addition to the storage-volume concept, the present invention also relies upon flow resistance elements within the chamber, which are stationary and non-operative. These elements favor blood flow in one direction only and thereby control the backflow of blood without reliance upon any operative components. It can be seen then that the present invention offers a number of significant advantages based on the foregoing over the known needle assemblies with operative valve arrangements included therein.

BRIEF DESCRIPTION OF THE DRAWINGS

FIG. 1 is a perspective view illustrating the preferred needle assembly with an anti-backflow feature of the present invention;

FIG. 2 is a cross-sectional view taken along line 2—2 of FIG. 1;

FIG. 3 is a cross-sectional view similar to the view of FIG. 2 but illustrating the needle assembly as it may appear during use;

FIG. 4 is a cross-sectional view of an alternative embodiment of the present invention;

FIG. 5 is a cross-sectional view illustrating another alternative embodiment of the present invention;

FIG. 6 is a cross-sectional view taken along line 6—6 of FIG. 5; and

FIG. 7 is a cross-sectional view taken along line 7—7 of FIG. 5.

DETAILED DESCRIPTION

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

Referring to the drawings, particularly to FIG. 1, there is illustrated the preferred embodiment of the needle assembly 10 of the present invention with anti-backflow features. The basic external components of needle assembly 10 include a housing 12, a first needle cannula 14 adapted for insertion into a patient and a second needle cannula 15 at the opposite end of housing 12, the second needle cannula adapted for penetration of an evacuated container for the collection of a blood sample. Housing 12 includes a threaded portion 18 adjacent second cannula 15 onto which a tubular holder for the evacuated container is threaded by mating threads at a forward end of the holder. Although this holder is not shown, these general aspects of multiple sample blood collections with this type of structure are well known to those skilled in this art.

In FIG. 2, the detailed construction of the internal components of needle assembly 10 is more clearly illustrated. Housing 12 has a forward end 24 and a rearward end 25, these ends being generally separable for ease of manufacturing and to better control the interior chamber to be formed. Forward end 24 is preferably cylindrically shaped and has a large bore 28 extending into and partially through its body. At the other end of this section, a smaller bore 29 does not extend completely through forward end to communicate with larger bore 28. However, a still smaller diameter channel 30 interconnects these two bores so that there is fluid communication from needle cannula 14 into larger bore 28. At the junction between bore 29 and channel 30, a shoulder 33 is formed. Needle cannula 14 abuts against this shoulder 33 for proper positioning. Once the needle cannula is in position it can be suitably affixed such as by adhesive means or the like. It is appreciated that the presence of channel 30 is not essential to the structure of this forward end of the housing, but is merely a preferable element. In addition, the size and diameter of channel 30 can be varied according to the choice of the manufacturer.

Forward end 24 of the housing also includes a number of longitudinal ribs 31 surrounding the outwardly extending cannula. A needle shield (not shown) generally covers the outwardly extending needle cannula and includes mating internal ribs within. The mating ribs between needle shield and needle assembly allow the user to facilitate the insertion or removal of the needle assembly into the tubular holder. Forward end 24 also includes an annular flange 32 which serves to provide a surface for joining the two portions of the housing together upon assembly. Once again, suitable fastening means, such as adhesives or the like, may be used to secure the two portions of the housing together.

Rearward end 25 includes a protruding portion 40, generally cylindrically shaped, and sized to fit within larger bore 28 of the forward end. At the opposite side of this rearward end, external threads 18 are provided as previously mentioned for providing a connection mechanism to the tube holder (not shown). A bore 41 extends partially through the rearward end of the housing which is substantially similar to bore 29 in the forward end of the housing. Once again, bore 41 is sized to accept the diameter of second needle cannula 15, which is secured to bore 41 by appropriate means, including adhesives and the like. A smaller diameter channel 42 communicates with bore 41 on one end, and terminates at the other end of protruding portion 40. Fluid is thus allowed to communicate between needle 15 and through rearward portion 25 by virtue of the communicating channel 42. An annular flange 46 is provided to cooperate with flange 32 in joining the two ends of the housing together. To assure proper fluid flow through the housing, an annular, elastomeric ring 48 is included around protruding portion 40. Upon assembling the forward end and the rearward end together, respective flanges 32 and 46 are secured by appropriate fastening means, such as adhesives and the like. Protruding portion 40 within larger bore 28 leaves an internal space forming a chamber 50 within the housing. Both channel 30 and channel 42 in the respective forward and rearward ends of the housing communicate with chamber 50. Although not shown for purposes of clarity, second needle cannula 15 may also be covered with a needle shield for protective and handling purposes. In addition, second needle cannula 15 may be covered with a flexible, elastomeric sheath if this second needle cannula is intended for multiple sample blood collection procedures.

In the preferred embodiment of this aspect of the invention, needle cannula 14 and needle cannula 15 are in substantial axial alignment on opposite sides of chamber 50, along the longitudinal axis of the housing, so that the respective cannulae are substantially parallel to the alignment axis. This needle assembly structure is intended to handle typical volumes of blood flow from a patient under normal conditions when acquiring blood samples. For instance, second needle cannula 15 is typically a 20 gauge needle and first needle cannula 14 could be 20, 21 or 22 gauge for different vein sizes and conditions. With this in mind, chamber 50 is designed so that it is sufficiently large to store blood therein collected from a patient. This blood storage is more clearly illustrated in FIG. 3. As can be seen in that FIG., when needle cannula 14 is inserted in a patient, and needle cannula 15 is inserted in an evacuated blood collection container, blood flows in the direction of the arrows, left to right in the illustration, from needle cannula 14 into chamber 50 and then through needle cannula 15 for proper collection. Should either pressure or flow conditions change so that the flow of blood would flow in the opposite direction, chamber 50 serves as a storage compartment with a large volume to provide a sufficiently long time lag before the blood can flow through in the reverse direction. Before blood can flow from channel 42 in the evacuated tube portion of the housing into channel 30 in the patient-facing portion of the housing, almost all of the volume of blood in chamber 50 must first be displaced. It has been found that with the typical and normal blood flow rates encountered in blood collecting procedures, a chamber volume of between four hundred (400) and six hundred (600) cubic millimeters should provide this backflow delay feature. A chamber volume of between four hundred (400) and five hundred (500) cubic millimeters is most preferred, inasmuch as this chamber size is large enough to delay backflow for a sufficiently long time lag under normal blood flow conditions, yet small enough to allow the needle assembly to be practical.

Turning now to FIG. 4, an alternative embodiment is illustrated which is a variation from the previously described embodiment. In this version, housing 60 is generally a one-piece structure with a bore 61 therethrough and including a threaded rear portion 62 for connection to a tube holder along the same lines as the previously described embodiment. Mounted in bore 61 is a dual diameter needle cannula 64 which includes a smaller diameter portion 65 and a larger diameter portion 66. Preferably, this dual diameter needle cannula is a one-piece, integrally formed structure with a neck portion 68 to provide a smooth continuity between smaller and larger portions. Smaller portion 65 includes an opening 69 in its end, and larger portion 66 also includes an opening 70 in its end. Accordingly, fluid is permitted to travel from the opening 69, which is normally inserted in the patient, through the needle assembly and out of opening 70, which is normally inserted in an evacuated blood collection container or similar device. In this embodiment, the interior portion of larger portion 66 provides a chamber 72 for the storage of blood collected from a patient. In addition, this larger portion also extends rearwardly to form the cannula portion which is adapted for penetration of an evacuated blood collection container.

Along these lines, the cross-sectional diameter of opening 70 is substantially equal to the cross-sectional diameter of chamber 72. However, cross-sectional diameter of smaller portion 65 is substantially smaller than the cross-sectional diameter of chamber 72. As in the previous embodiment, the larger diameter portion of this needle cannula forms a sufficiently large chamber to delay backflow of blood into the patient. This chamber volume is in the range of three hundred (300) to six hundred (600) cubic millimeters, with the preferable range being four hundred (400) to five hundred (500) cubic millimeters for compatible size purposes.

Another embodiment of the present invention is illustrated in FIGS. 5-7. In this embodiment, the basic needle assembly structure is similar to the needle assembly described with respect to FIGS. 1-3. Accordingly, like reference numbers will be used to refer to corresponding components. Chamber 50a in the embodiment of FIG. 5, however, does not require a specific volume in order to render the anti-backflow features. Chamber 50a includes a number of objects therein in order to provide flow resistance in the flow of blood from chamber 50a toward channel 30a. These objects preferably take the form of tapered cones 80 which are positioned within chamber 50a so that their narrow, tapered portions face toward channel 30a. These cones are mounted on a longitudinal bore 81 in substantially concentric fashion so that the cones will be substantially centrally mounted within the chamber in order to leave an annular clearance therearound for flow of blood. In order to fix bore 81 in position, one or more circular plates 82 are provided. Bore 81 is attached to the inside diameter of plate 82, while the peripheral surface of plate 82 is connected to the interior wall of housing end 24a. These attachments can be made by various adhesive means or the like. As seen more clearly in FIG. 7, each circular plate 82 has one or more holes 84 therethrough so that blood can pass through the plate. The holes in different circular plates 82 can be staggered or offset from adjacently lying plates so that even greater resistance to blood flow is provided. It can be seen, especially in FIG. 5, that blood flow will travel favorably in the direction of the arrows, from left to right in the illustration. However, the structure and orientation of cones 80, circular plates 82 and holes 84 therethrough all contribute to rendering backflow resistance if the blood tends to flow in the opposite direction. It is to be appreciated that other configurations of flow resistance elements fall within the purview of this aspect of the invention. Non-operative components are employed for these flow resistance elements which do not rely upon the open/close requirements of valve elements previously known and used. The flow resistance components used herein are preferably rigid in nature and shaped and oriented to favor blood flow in one direction only. The choice of materials, shapes, quantity and orientation of these flow resistance elements are left to the designer as long as they are compatible with the objects of this invention.

In all embodiments of the present invention, a flexible, pierceable, elastomeric sheath may be placed over the needle which is intended to pierce a stopper in an evacuated blood collection tube. This sheath, not shown in the drawings, serves as a valve so that the needle assembly may be used in collecting multiple samples from a patient. Such a valve sheath is described in U.S. Pat. No. 3,469,572.

Thus, the present invention provides a needle assembly with anti-backflow features which do not rely upon operative valve elements in order to be functional. The employment of the structure as described in conjunction with this invention offers a number of advantages over the valve type needles assemblies heretofore relied upon.

What is claimed is:

1. A needle assembly for use in resisting backflow of blood being collected from a patient comprising:
   a housing having a forward end, a rearward end and a chamber therein;
   a first access opening through the forward end of said housing in fluid communication with said chamber;
   a cannula extending outwardly from said first access opening in fluid communication with said chamber and being adapted for insertion in a patient;
   a second access opening through the rearward end of said housing in fluid communication with said chamber adapted for communication with collection means for receiving said blood; and
   means positioned in said chamber to provide flow resistance to the flow of blood from said chamber toward said first access opening, said flow resistance means including a plurality of substantially rigid, non-operative objects within said chamber to limit the flow area of blood within said chamber, said objects including tapered cones being substantially centrally mounted within said chamber while leaving annular clearance for blood to flow therearound, said cones positioned so that their narrow, tapered portions face toward said first access opening whereby flow of blood is favored in the direction from said first access opening into said chamber and is resisted in the opposite direction.

2. A needle assembly for use in resisting backflow of blood being collected from a patient comprising:
   a housing having a forward end, a rearward end and a chamber within;
   a first access opening through the forward end of said housing in fluid communication with said chamber;
   a first cannula extending from said first access opening in fluid communication with said chamber and being adapted for insertion into a patient;
   a second access opening through the rearward end of said housing in fluid communication with said chamber, said first and said second openings being in substantial alignment on opposite sides of said chamber;
   a second cannula extending from said second access opening in fluid communication with said chamber and being adapted for penetration of an evacuated container for collection of a blood sample; and
   a plurality of tapered cones substantially centrally mounted in said chamber along a longitudinal axis thereof, with annular clearance for blood to flow therearound, said cones being positioned so that their narrow, tapered portions face toward said first access opening whereby flow of blood is favored in the direction from said first access opening into said chamber and is resisted in the opposite direction.

* * * * *